United States Patent [19]

Jenks et al.

[11] 4,146,718
[45] Mar. 27, 1979

[54] ALKYL 5,6-DICHLORO-3,4-DIHYDRO-2(1H)-IMINOQUINAZOLINE-3-ACETATE HYDROHALIDES

[75] Inventors: Thomas A. Jenks, Liverpool, N.Y.; Warren N. Beverung, Jr., Fairfax, Va.; Richard A. Partyka, Liverpool, N.Y.

[73] Assignee: Bristol-Myers Company, New York, N.Y.

[21] Appl. No.: 894,464

[22] Filed: Apr. 10, 1978

[51] Int. Cl.² ............................................ C07D 239/84
[52] U.S. Cl. ................................. 544/292; 260/570.9; 260/575; 544/250
[58] Field of Search ........................................ 544/292

[56] References Cited
U.S. PATENT DOCUMENTS 3,932,407   1/1976   Beverung et al. .................. 544/250

Primary Examiner—Paul M. Coughlan, Jr.
Attorney, Agent, or Firm—Richard R. Lloyd

[57] ABSTRACT

The known blood platelet antiaggregative agent 6,7-dichloro-1,5-dihydroimidazo[2,1-b]quinazolin-2(3H)-one is prepared in high yield via an improved process involving a novel intermediate of the Formula

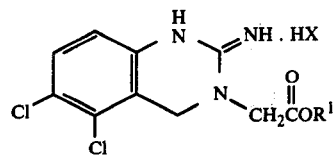

in which $R^1$ is (lower)alkyl and X is bromo, chloro or iodo. Two processes for the preparation of compounds of the Formula III are disclosed, one of which involves the novel intermediate

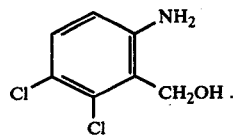

16 Claims, No Drawings

ALKYL 5,6-DICHLORO-3,4-DIHYDRO-2(1H)-IMINOQUINAZOLINE-3-ACETATE HYDROHALIDES

SUMMARY OF THE INVENTION

This application relates to a new and improved process for the preparation of the known blood platelet antiaggregative compound 6,7-dichloro-1,5-dihydroimidazo[2,1-b]quinazolin-2(3H)-one of Formula I

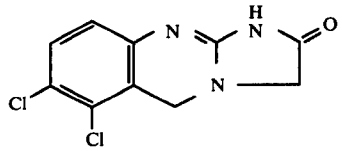

from a (lower)alkyl N-(6-amino-2,3-dichlorobenzyl)glycine of Formula II

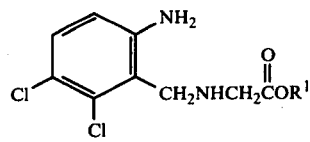

in which $R^1$ is (lower)alkyl, via a novel (lower)alkyl 5,6-dichloro-3,4-dihydro-2(1H)-iminoquinazoline-3-acetate hydrohalide intermediate of Formula III

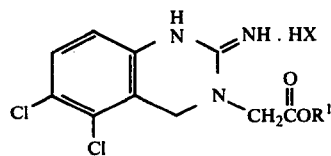

in which $R^1$ is (lower)alkyl and X is bromo, chloro or iodo.

DESCRIPTION OF THE PRIOR ART

U.S. Pat. No. 3,932,407 discloses compounds of the formula

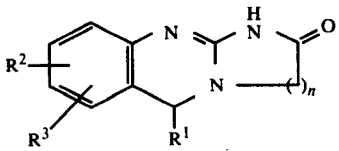

in which $R^1$ is H, phenyl or (lower)alkyl, $R^2$ and $R^3$ when alike are H, chloro, bromo, fluoro, (lower)alkyl, hydroxy or (lower)alkoxy, $R^2$ and $R^3$ when different are H, chloro, bromo, fluoro, $SO_3H$, $CF_3$, hydroxy, nitro, amino, phenyl, (lower)alkyl of 1 to 3 carbon atoms or (lower)alkoxy of 1 to 3 carbon atoms, or when taken together $R^2$ and $R^3$ are methylenedioxy or the residue of a phenyl ring, and n is an integer of 1 or 2; and pharmaceutically acceptable acid addition salts thereof. The compounds, which are disclosed as hypotensive, blood platelet antiaggregative and/or bronchodilator agents, are prepared inter alia by a multistep process ending the reaction of CNBr with an ethanol solution of a compound of the formula

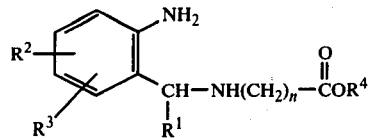

in which $R^1$, $R^2$, $R^3$ and n are as described above, and $R^4$ is (lower)alkyl. Although the above patent generically discloses the compound of Formula I as being prepared by the above process, its preparation is specifically exemplified only by chlorination of the compound of the formula

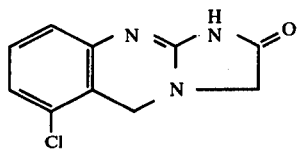

COMPLETE DISCLOSURE

When a compound of Formula II is reacted in alcoholic solution with CNBr according to the prior art process, the compound of Formula I is formed directly. We have unexpectedly found that much higher yields of Compound I may be obtained by reacting Compound II with CNBr, CNCl or CNI in an inert, aprotic organic solvent and isolating the novel intermediate of Formula III. Intermediate III is then treated with a base to produce the compound of Formula I. Surprisingly, the yield of Compound I obtained in this two-step procedure typically is about four times greater than the yield obtained in the one-step process.

According to one embodiment of the present invention there is provided a compound of the formula

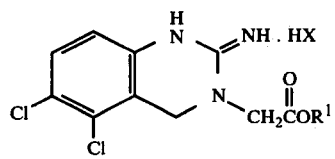

wherein $R^1$ is (lower)alkyl and X is chloro, bromo or iodo. In a preferred embodiment X is bromo and $R^1$ is methyl, ethyl, n-propyl, isopropyl or n-butyl. In a more preferred embodiment X is bromo and $R^1$ is methyl, ethyl or n-propyl. In a most preferred embodiment X is bromo and $R^1$ is ethyl.

According to another embodiment of the present invention there is provided a process for the preparation of a compound of the Formula

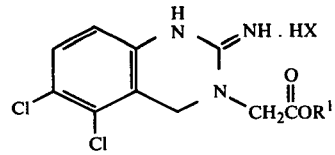

wherein $R^1$ is (lower)alkyl and X is chloro, bromo or iodo, which process comprises reacting a compound of the Formula

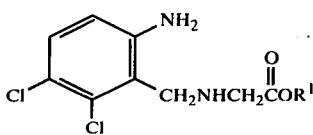

wherein R[1] is as defined above with a compound of the Formula CNX wherein X is as defined above, in an aprotic, reaction-inert organic solvent, at a temperature up to about 200°. A preferred temperature range is from about 50° to about 150° and a more preferred range is from about 80° to about 120°. It is preferred to use at least one mole of CNX per mole of Compound II and it is more preferred to use about an equimolar amount.

Suitable aprotic, reaction-inert, organic solvents for use in this reaction will be apparent to those skilled in the art. Such solvents include benzene, toluene, xylene, hexane, heptane, octane, nonane, 2,2,4-trimethylpentane, cyclopentane, cyclohexane, cycloheptane, tetrahydrofuran, dioxane, chloroform, carbon tetrachloride, di-n-propyl ether and di-n-butyl ether. A preferred solvent is toluene.

Intermediate III is readily converted to the compound of Formula I by reaction with about an equimolar amount of a base, and preferably an organic base, and most preferably a tertiary amine such as triethylamine, N,N-dimethylaniline or the like. The reaction is conducted in an non-reactive solvent and preferably in a (lower)alkanol such as ethanol, propanol, 2-methoxyethanol or the like.

Preparation of Starting Materials

The preparation of starting compounds of Formula II by two different routes is given below, as exemplified by the preparation of the compound of Formula II in which R[1] is ethyl.

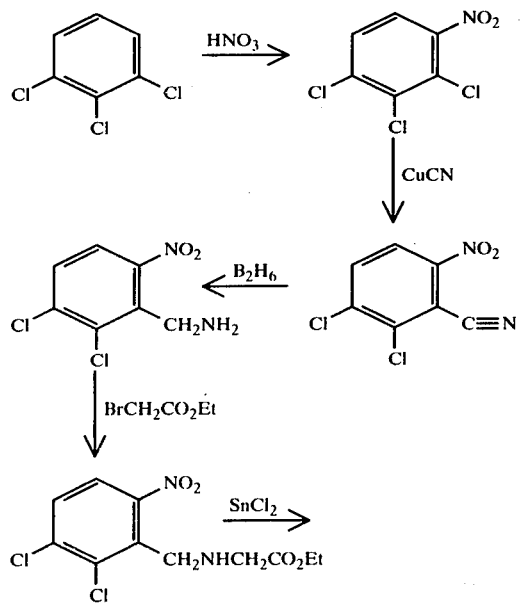

Reaction Scheme A

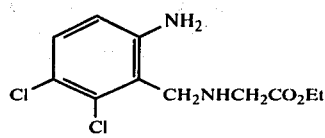

2,3,4-Trichloronitrobenzene

A 12 liter resin pot equipped with an efficient mechanical stirrer and a thermometer was charged with 90% (sp. gr. 1.4826) nitric acid (3.6 liters). An iced-water bath was used to keep the temperature between 25° and 30° while 1,2,3-trichlorobenzene (1.89 kg, 10.4 mol) was added in portions over 30 minutes. The resulting mixture was stirred for 30 minutes and then poured into a 9.5 liter battery jar equipped with an efficient stirrer and containing about 5 kg of ice. The resulting solid was filtered off and washed well with water.

This solid cannot be dried in a vacuum oven because it sublimes. Therefore, it was taken up in $CH_2Cl_2$ (about 3 liters) and the water layer was separated. The $CH_2Cl_2$ solution was washed with water (500 ml) and with saturated aqueous NaCl (500 ml), and then dried over $MgSO_4$. The drying agent was filtered off and the filtrate was concentrated in vacuo. Before the residue solidified it was poured into a crystallizing dish. Then it was dried in a desiccator at ca. 1 mm Hg pressure over $P_2O_5$. Yield 2237 g (95%); mp. 52°–54.5°.

2,3-Dichloro-6-nitrobenzonitrile

Under a nitrogen atomosphere, pyridine (42 ml, 0.52 mol) was spread evenly over a mixture of 2,3,4-trichloronitrobenzene (225 g, 1 mol) and cuprous cyanide (89.6 g, 1 mol). The mixture was heated to 100° and held at this temperature until it became stirrable. Then the stirred mixture was heated to 165° over 1.5 hours, and held at this temperature for 30 minutes. The dark mixture was allowed to cool, then concentrated HCl (500 ml) and toluene (250 ml) were added. The mixture was vigorously stirred for 1.5 hours. The layers were separated and the aqueous phase was extracted with toluene (3 × 250 ml). The combined toluene extracts were washed with concentrated HCl (3 × 250 ml), water (250 ml) and saturated aqueous NaCl (2 × 250 ml). The toluene solution was dried over $Na_2SO_4$, filtered and stripped to obtain 185 g (85%) of the title benzonitrole. The product was 87% pure and contained about 7% trichloronitrobenzene. Recrystallization from methanol (2.1 ml/g) gave a product of 99% purity.

2,3-Dichloro-6-nitrobenzylamine

To a solution of recrystallized 2,3-dichloro-6-nitrobenzonitrile (434 g, 2 mol) in tetrahydrofuran (THF) (2.4 liters), under $N_2$, was added a solution of borane in THF (4 liters of a 1 molar solution). The addition was made over about 1.25 hours and the reaction temperature rose to 61° (reflux). The solution was refluxed for 2 hours after the addition was complete.

The solution was cooled to 16° and 1 liter of water added. The addition was made very cautiously at first because the first few milliliters of water produced a lot of foam. Then concentrated HCl (470 ml) was added and the solution was stirred overnight.

The solution was concentrated in vacuo to remove THF, filtered and the residue washed with diethyl ether. The filtrate was extracted with diethyl ether (3 × 500 ml). Then the aqueous solution was chilled and basified (pH 8) with 40% aqueous NaOH (about 600 ml). The alkaline solution was extracted with diethyl ether (3 × 500 ml). The ethereal extracts were combined and washed with H₂O (250 ml), then with saturated aqueous NaCl (250 ml) and then dried over Na₂SO₄. Filtration and evaporation of the solvent gave 305 g (69%) of the title product as an orange, crystalline solid. Gas chromatography indicated that the product was about 77% pure, but it was used as such in the next step. An analytical sample of the above product (obtained via purification of its hydrochloride) melted at 51°–53°.

Ethyl N-(2,3-dichloro-6-nitrobenzyl)glycine hydrochloride

A solution of ethyl bromoacetate (157 ml, 1.41 mols) in dioxane (1 liter) was added dropwise to a refluxing solution of 2,3-dichloro-6-nitrobenzylamine (306.2 g, 1.38 mols) and triethylamine (193 ml, 1.38 mols) in dioxane (1 liter). The addition took 2 hours and the mixture was refluxed for 16 hours after the addition was complete. The cooled mixture was filtered to remove TEA.HBr, the residue was washed with dioxane and the filtrate and washings were combined and stripped of solvent. The residue was suspended in absolute ethanol (2 liters) and the mixture was cooled in an iced water bath while being saturated with gaseous HCl. Anhydrous ether (2 liters) was added and the resulting mixture was stirred for about 1 hour, then filtered. The residue was washed with anhydrous ether, then dried under pump vacuum (0.5–1 mm Hg). A yield of 238 g (50%) was obtained. Chromatography of the free base showed no contaminants. An analytical sample, obtained by recrystallization from an ethanol-ether mixture, melted at 203°–205°.

N-(6-Amino-2,3-dichlorobenzyl)glycine Ethyl Ester

A solution of stannous chloride dihydrate (1051.4 g., 5.06 mol) in concentrated HCl (3.8 liters) was added briskly (35 minutes) to a cooled solution of ethyl N-(2,3-dichloro-6-nitrobenzyl)glycine hydrochloride (344 g., 1.00 mol) in concentrated HCl (2.8 liters). The temperature was held at 22° ± 5° during the addition. The mixture was slowly (approximately 0.5 hour) heated to 40° after the addition and held at that temperature for one hour. After being stirred briefly without being heated the mixture was cooled to 15° and then filtered through a sintered glass filter. The residue was washed with a little ice cold water.

The solid was suspended in water (3.5 liters) and the mixture basified with ammonium hydroxide while being chilled in an iced water bath. The resulting mixture was extracted with ether (3 × 1 liter). The ether extracts were combined and washed with water (250 ml) and saturated aqueous NaCl (250 ml) and then dried over Na₂SO₄. Filtering and stripping gave 242 g. (87%) of the title product, mp 56°–60°. This material was 92% pure by chromatography.

Reaction Scheme B

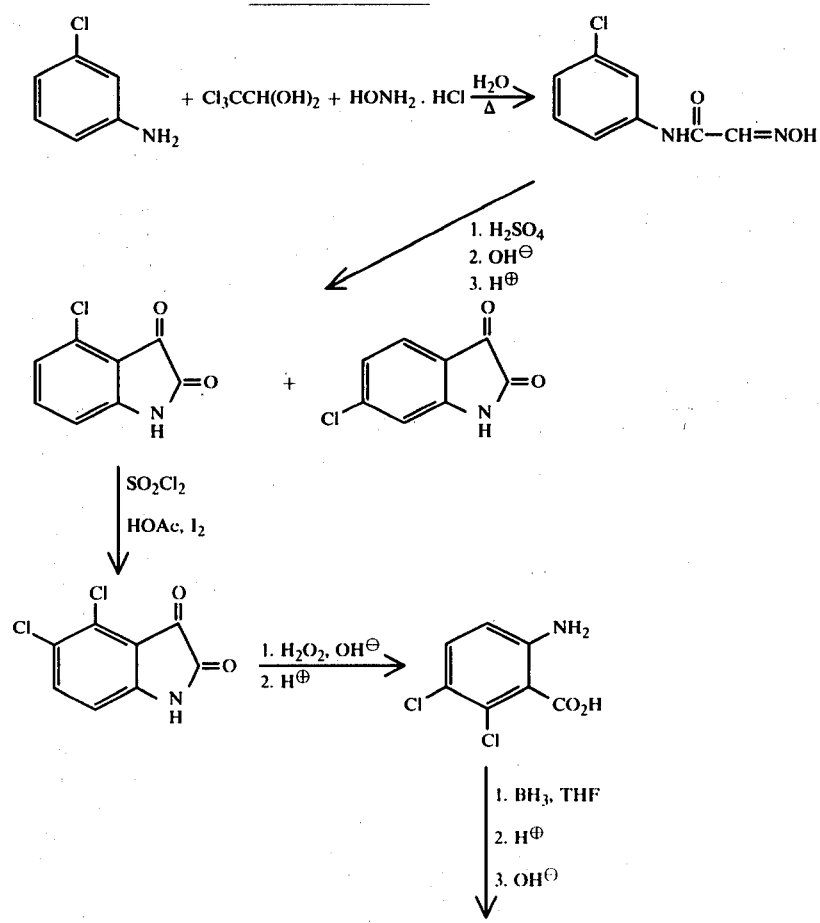

Reaction Scheme B

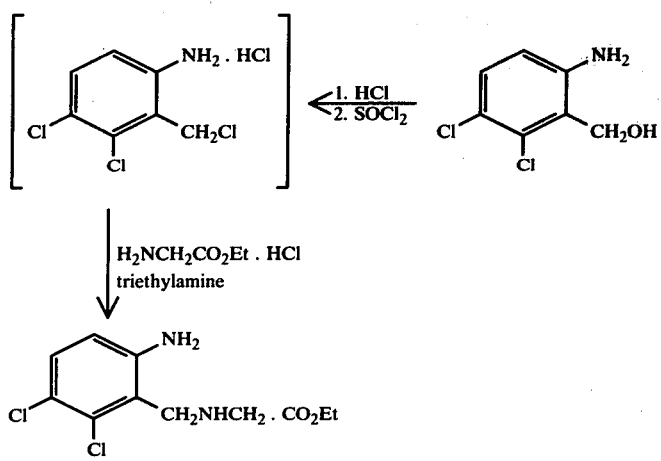

iso-Nitroso-m-chloroacetanilide

This material was prepared in 91% yield by the procedure of A. E. Senear, et al., J. Am. Chem. Soc., 68, 2695 (1946).

4-Chloroisatin

A mixture of the 4-chloro and 6-chloro isomers was prepared by the procedure of Senear, et al., above. After separation of the isomers by the method of P. W. Sadler, J. Org. Chem., 21, 169 (1956), recrystallization of 4-chloroisatin from ethanol gave a 23% yield of product. In a large scale run, the 4-chloro isomer was obtained in 42% yield and did not require recrystallization.

4,5-Dichloroisatin

Chlorination of 4-chloroisatin with sulfuryl chloride by the method of B. R. Baker, et al., J. Org. Chem., 17, 149 (1952), gave a 70% yield of the title compound.

5,6-Dichloroanthranilic Acid

This material was obtained from 4,5-dichloroisatin in 91% yield by the method of B. R. Baker, et al., J. Org. Chem., 17, 141 (1952).

6-Amino-2,3-Dichlorobenzyl Alcohol

A solution of borane (0.55 mol) in 550 ml of tetrahydrofuran was slowly added, over a period of 1 hour, to a solution of 5,6-dichloroanthranilic acid (44.5 g, 0.216 mol) in tetrahydrofuran (1200 ml). The solution was heated at reflux for 18 hours, cooled and treated slowly with 550 ml of 1N HCl. The tetrahydrofuran was removed in vacuo at 30° and the aqueous mixture was washed with ether and then made basic with concentrated $NH_4OH$. The resulting solid was extracted with ether, dried ($K_2CO_3$) and the solvent was evaporated to leave 31.5 g. (76%) of the title compound as light pinkish needles, m.p. 133.5°–135°. An analytical sample was prepared by recrystallization from benzene; white needles, m.p. 134°–135.5°.

Calcd. for $C_7H_7Cl_2NO$: C, 43.78; H, 3.67; N, 7.30. Found: C, 43.79; H, 3,87; N, 7.17.

N-(6-Amino-2,3-dichlorobenzyl)glycine Ethyl Ester

A solution of 6-amino-2,3-dichlorobenzyl alcohol (10.0 g., 0.0521 mol) in 250 ml. of boiling benzene was treated with a slow-stream of dry hydrogen chloride for 0.5 hour. The finely divided suspension was cooled slightly, thionyl chloride (12.4 g, 0.104 mol) was added in one portion, and reflux was continued for 2.5 hours. The solution was evaporated in vacuo to remove excess thionyl chloride and hydrogen chloride, and the residue was redissolved in 250 ml. benzene. This solution was added over 1 hour to a refluxing mixture of glycine ethyl ester hydrochloride (29.1 g, 0.208 mol) and triethylamine (31.6 g, 0.313 mol) in 600 ml. $CH_2Cl_2$. Reflux was continued for 1 hour, the mixture was allowed to stand overnight and was then extracted with 1N HCl. The extract was washed with $CH_2Cl_2$ and ether, made slightly alkaline with concentrated $NH_4OH$ and extracted with ether. After drying ($K_2CO_3$) and evaporation there remained 8.3 g (58%) of the title product as a light yellow oil which crystallized. The analytical sample was obtained from Skellysolve B as white needles, mp. 60°–61° C.

Calcd. for $C_{11}H_{14}Cl_2N_2O_2$: C, 47.67; H, 5.09; N, 10.11. Found: C, 47.75; H, 5.18; N, 10.34.

COMPARATIVE PREPARATION 1

6,7-Dichloro-1,5-dihydroimidazo[2,1-b]quinazolin-2(3H)-one Hydrochloride Prepared Via The One-Step Prior Art Procedure A solution of cyanogen bromide (3.2 g, 0.030 mol) in 100 ml. 2-methoxyethanol was added to a solution of N-(6-amino-2,3-dichlorobenzyl)glycine ethyl ester (8.2 g, 0.030 mol) in 250 ml. 2-methoxyethanol. The solution was stirred at room temperature for 1 hour, heated at reflux for 22 hours, and cooled. The precipitate was filtered off, washed with ether and air dried to give 3.11 gms. of the crude title product (31% yield as the hydrobromide salt). Recrystallization from ethanolic HCl gave the pure title product in 71% recovery (22% overall yield); m.p. >250°.

Calcd. for $C_{10}H_7Cl_2N_3O\cdot HCl\cdot 0.5H_2O$: C, 39.82; H, 3.01; N, 13,93. Found: C, 39.58; H, 3.19; N, 13.32.

As stated above, the compound of Formula I is a known blood platelet antiaggregative agent. Table I compares the activities of the compound of Formula I and other known blood platelet antiaggregative agents in various antiaggregative and antithrombosis tests. Although the compounds of Formula III are primarily intended as intermediates in the preparation of the compound of Formula I, they themselves have blood platelet antiaggregative properties. For comparison purposes, one of the compounds of Formula III ($R^1$ = ethyl, X = bromo) is included in Table I. The tests referred to in Table I were conducted as set out in detail in J. S. Fleming, et al., Journal of Pharmacology and Experimental Therapeutics, 194, 435 (1975).

SLIDE II

Antiaggregative and Antithrombosis Tests in Various In Vitro, Ex Vivo And In Vivo Experimental Systems

| Compound | Aggregometry - Rabbit - PRP | | | | In Vivo Animal Models ED50's (mg/kg) | | |
|---|---|---|---|---|---|---|---|
| | In Vitro EC50 ($\mu$g/ml) | | Ex Vivo ED50 (mg/kp ip) | | Rabbit Biolaser Thrombosis | Dog Electrical Thrombosis | Rat Endotoxin Shock |
| | ADP | Collagen | ADP | Collagen | | | |
| Aspirin | >512 | 7 | >100 | 3 | >60 iv | 50 po | >256 po |
| Dipyridamole | >512 | 245 | >100 | >100 | >60 iv | >35 ip | >256 po |
| Sulfinpyrazone | >512 | 62 | >100 | 3 | >60 iv | >100 po | >128 po |
| Compound I | 0.3 | 0.08 | 1.25 | 1 | 2.5 po | 1.5 po | 25 po |
| Compound III ($R^1$ = ethyl, X = Br) | 9 | 3.6 | Not Tested | — | — | — | — |

PRP = Platelet-rich plasma
ADP = Adenosine diphosphate

As used herein, the term (lower)alkyl refers to a straight or branched chain alkyl group containing from 1 to 6 carbon atoms. All temperatures given herein are in degrees centigrade.

The following examples illustrate, but in no way limit, the present invention.

EXAMPLE 1

Ethyl 5,6-Dichloro-3,4-dihydro-2(1H)-iminoquinazoline-3-acetate Hydrobromide

A solution of cyanogen bromide (0.53 gm. 5 mmol) in toluene (10 ml.) was added to a solution of N-(6-amino-2,3-dichlorobenzyl)glycine ethyl ester (1.39 gm, 5 mmol) in toluene (10 ml.) and stirred at room temperature. There was an almost immediate precipitate. Stirring was continued for 30 minutes, and the reaction mixture was then heated to reflux and refluxed for 18 hours. After cooling, the solid was filtered off, washed with toluene and dried to give 1.81 gm (94.5%) of the title product. A portion of the product was recrystallized from ethanol, washed with ethanol and ether, and dried in vacuo at 78° to give an analytical sample as golden crystals.

Calcd. for $C_{12}H_{13}Cl_2N_3O_2 \cdot HBr$: C, 37.62; H, 3.68; N, 10.97. Found: C, 37.59; H, 3.57; N, 10.80.

EXAMPLE 2

Ethyl 5,6-Dichloro-3,4-dihydro-2(1H)-iminoquinazoline-3-acetate Hydrobromide

A solution of cyanogen bromide (89.6 g, 0.85 mol) in toluene (1.6 liters) was poured into a solution of N-(6-amino-2,3-dichlorobenzyl)glycine ethyl ester (231 g, 0.834 mol) in toluene (1.6 liters). The temperature rose quickly from 18° to 31°. The mixture was slowly (1 hour) heated to reflux and refluxed for 12 hours. The mixture was cooled to room temperature and filtered, the product being washed with toluene both by decantation and on the filter. The residue was washed with ether and then dried under pump vacuum (0.5-1 mm Hg) over $P_2O_5$. A yield of 290 g (91%) of the title product was obtained as a brown powder. When heated this powder decomposed over a wide temperature range: 200°-300°.

Its infrared and nmr spectra were consistent with the desired product. Infrared peaks were at 3140 (broad), 1745 (—C=O), 1661 (—C=N—), 1636, 1550, 1471 and 1215 cm$^{-1}$. Nmr peaks (TMS standard) were at δ 8.24 (broads s), 7.25 (AB, q, 2H), 4.69 (s, 2H), 4.55 (s, 2H), 4.27 (q, 2H) and 1.32 (t, 3H).

EXAMPLE 3

6,7-Dichloro-1,5-dihydroimidazo[2,1-b]quinazolin-2(3H)-one

A mixture of ethyl 5,6-dichloro-3,4-dihydro-2(1H)-iminoquinazoline-3-acetate hydrobromide (289.6 g, 0.756 mol), absolute ethanol (4.5 liters) and triethylamine (106 ml, 0.758 mol) was refluxed for 4 hours. The mixture was cooled and as much of the ethanol as possible decanted off. The solid was suspended in fresh absolute ethanol and, after the mixture was stirred for 0.5 hour, filtered off. Then the solid was suspended in a mixture of absolute ethanol (600 ml.) and 95% ethanol (2.4 liters) and refluxed for 4 hours. The mixture was filtered while warm. The solid was dried under pump vacuum (0.5-1 mm Hg) over $P_2O_5$. This gave 179 g (92%) of the title product as an ivory colored solid.

Infrared peaks were at 1702 (weak), 1638, 1554, 1468, and 1440 cm$^{-1}$. Nmr peaks (TFA) were at δ 7.33 (AB, q, 2H), 4.97 (s, 2H) and 4.59 (s, 2H).

EXAMPLE 4

6,7-Dichloro-1,5-dihydroimidazo[2,1-b]quinazolin-2(3H)-one Monohydrochloride Monohydrate 6,7-Dichloro-1,5-dihydroimidazo[2,1-b]-quinazolin-2(3H)-one (94.0 g, 0.367 mol) was added to 2.82 liters of boiling methanol. To the suspension was added 77 ml. (0.92 mol) of concentrated hydrochloric acid. A nearly complete solution resulted. Darco G-60 was added, the mixture was boiled for ca. 3 minutes and then filtered. The filtrate was reheated to boiling to effect solution, then cooled slightly, and 1.9 liters of ether added cautiously. The mixture was stirred at ambient temperature for 2 hours and the solid was filtered off. (Crop A).

Some material tended to crystallize in the funnel during the charcoal treatment step; the charcoal and solids therefore were suspended in hot methanol and filtered. This filtrate was combined with the filtrate from Crop A, and the combined filtrates were concentrated in vacuo to about 1.3 liters and heated to boiling to effect complete solution. After filtration and slight cooling, 800 mls. of ether were added and the mixture was stirred at room temperature for 1 hour. The resulting solid was filtered off (Crop B). Chromatography showed both crops to be of very high purity. They were combined and dried in vacuo (ca. 1 mm Hg) overnight. Total weight of product was 88.1 gm. Karl Fischer analysis indicated 2.27% water. The material was placed in a desiccator over saturated aqueous $Ca(NO_3)_2$ (ca. 50% relative humidity) and analyzed for water daily. After 4 days analysis showed 5.64% water (5.80% theoretical for monohydrate). The weight of product was 91.9 gm (80.6% of theoretical).

EXAMPLE 5

The general procedure of Example 1 is repeated, except that the cyanogen bromide utilized therein is replaced by an equimolar amount of cyanogen chloride, and there is thereby produced ethyl 5,6-dichloro-3,4-dihydro-2(1H)-iminoquinazoline-3-acetate hydrochloride.

EXAMPLE 6

The general procedure of Example 1 is repeated, except that the cyanogen bromide utilized therein is replaced by an equimolar amount of cyanogen iodide, and there is thereby produced ethyl 5,6-dichloro-3,4-dihydro-2(1H)-iminoquinazoline-3-acetate hydroiodide.

EXAMPLE 7

The general procedure of Example 1 is repeated, except that the N-(6-amino-2,3-dichlorobenzyl)glycine ethyl ester utilized therein is replaced by an equimolar amount of N-(6-amino-2,3-dichlorobenzyl)glycine methyl ester,
N-(6-amino-2,3-dichlorobenzyl)glycine n-propyl ester,
N-(6amino-2,3-dichlorobenzyl)glycine isopropyl ester and
N-(6-amino-2,3-dichlorobenzyl)glycine n-butyl ester, respectively, and there is thereby produced methyl 5,6-dichloro-3,4-dihydro-2(1H)-iminoquinazoline-3-acetate hydrobromide,
n-propyl 5,6-dichloro-3,4-dihydro-2(1H)-iminoquinazoline-3-acetate hydrobromide,
isopropyl 5,6-dichloro-3,4-dihydro-2(1H)-iminoquinazoline-3-acetate hydrobromide and
n-butyl 5,6-dichloro-3,4-dihydro-2(1H)-iminoquinazoline-3-acetate hydrobromide, respectively.

EXAMPLE 8

The general procedure of Example 5 is repeated, except that the N-(6-amino-2,3-dichlorobenzyl)glycine ethyl ester utilized therein is replaced by an equimolar amount of N-(6-amino-2,3-dichlorobenzyl)glycine methyl ester,
N-(6-amino-2,3-dichlorobenzyl)glycine n-propyl ester,
N-(6-amino-2,3-dichlorobenzyl)glycine isopropyl ester and
N-(6-amino-2,3-dichlorobenzyl)glycine n-butyl ester, respectively, and there is thereby produced methyl 5,6-dichloro-3,4-dihydro-2(1H)-iminoquinazoline-3-acetate hydrochloride,
n-propyl 5,6-dichloro-3,4-dihydro-2(1H)-iminoquinazoline-3-acetate hydrochloride,
isopropyl 5,6-dichloro-3,4-dihydro-2(1H)-iminoquinazoline-3-acetate hydrochloride and
n-butyl 5,6-dichloro-3,4-dihydro-2(1H)-iminoquinazoline-3-acetate hydrochloride, respectively.

EXAMPLE 9

The general procedure of Example 6 is repeated, except that the N-(6-amino-2,3-dichlorobenzyl)glycine ethyl ester utilized therein is replaced by an equimolar amount of N-(6-amino-2,3-dichlorobenzyl)glycine methyl ester,
N-(6-amino-2,3-dichlorobenzyl)glycine n-propyl ester,
N-(6-amino-2,3-dichlorobenzyl)glycine isopropyl ester and
N-(6-amino-2,3-dichlorobenzyl)glycine n-butyl ester, respectively, and there is thereby produced methyl 5,6-dichloro-3,4-dihydro-2(1H)-iminoquinazoline-3-acetate hydroiodide,
n-propyl 5,6-dichloro-3,4-dihydro-2(1H)-iminoquinazoline-3-acetate hydroiodide,
isopropyl 5,6-dichloro-3,4-dihydro-2(1H)-iminoquinazoline-3-acetate hydroiodide and
n-butyl 5,6-dichloro-3,4-dihydro-2(1H)-iminoquinazoline-3-acetate hydroiodide, respectively.

We claim:

1. A compound of the formula

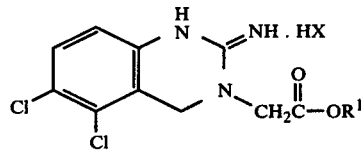

wherein $R^1$ is (lower)alkyl and X is chloro, bromo or iodo.

2. A compound of claim 1 wherein X is chloro.
3. A compound of claim 1 wherein X is bromo.
4. A compound of claim 1 wherein X is iodo.
5. A compound of claim 1 wherein $R^1$ is methyl.
6. A compound of claim 1 wherein $R^1$ is ethyl.
7. A compound of claim 1 wherein $R^1$ is n-propyl.
8. A compound of claim 1 wherein $R^1$ is isopropyl.
9. A compound of claim 1 wherein $R^1$ is n-butyl.
10. The compound of the formula

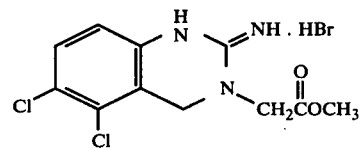

11. The compound of the formula

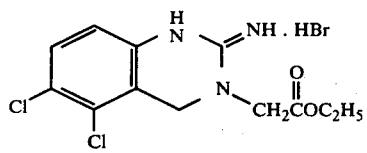

12. The compound of the formula

13. The compound of the formula
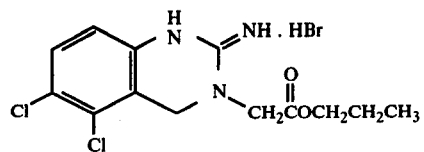
14. The compound of the formula
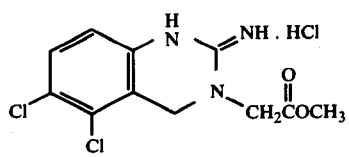
15. The compound of the formula
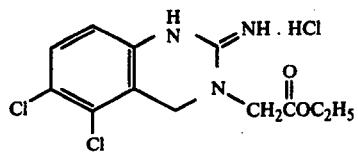
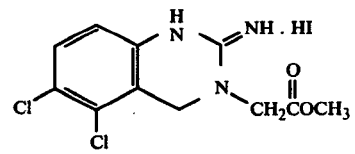
16. The compound of the formula
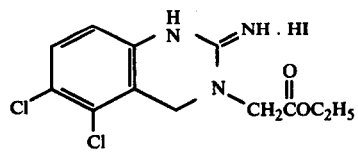
* * * * *

UNITED STATES PATENT AND TRADEMARK OFFICE
CERTIFICATE OF CORRECTION

PATENT NO. : 4,146,718
DATED : March 27, 1979
INVENTOR(S) : Thomas A. Jenks et al.

It is certified that error appears in the above-identified patent and that said Letters Patent are hereby corrected as shown below:

In column 9, line 7, "SLIDE II" should read:

---TABLE I---.

Signed and Sealed this

Eighteenth Day of September 1979

[SEAL]

Attest:

LUTRELLE F. PARKER

Attesting Officer     Acting Commissioner of Patents and Trademarks